United States Patent [19]

Ashbury et al.

[11] Patent Number: 4,601,711
[45] Date of Patent: Jul. 22, 1986

[54] SYRINGE HOLDER DEVICE FOR CONTROLLED FORCE AMPLIFICATION SYRINGE FLUID FLOW

[76] Inventors: Thomas W. Ashbury, P.O. Box 274, Flint, Mich. 48501; Gerald J. Wadsworth, 2810 Delta River Dr., Lansing, Mich. 48906

[21] Appl. No.: 686,003

[22] Filed: Dec. 24, 1984

[51] Int. Cl.$^4$ .............................................. A61M 5/00
[52] U.S. Cl. ...................................... 604/224; 604/187
[58] Field of Search ............... 604/187, 207, 208, 211, 604/224, 228, 407; 222/386, 390

[56] References Cited

U.S. PATENT DOCUMENTS 3,720,211  3/1973  Kyrias ................................. 604/155
4,397,647  8/1983  Gordon ....................... 128/DIG. 26 X
4,465,478  8/1984  Sabelman et al. ..................... 604/224

FOREIGN PATENT DOCUMENTS 2493151  5/1982  France .................................... 604/155
 401253  2/1932  United Kingdom ................ 604/224

Primary Examiner—Stephen C. Pellegrino
Attorney, Agent, or Firm—Krass & Young

[57] ABSTRACT

Apparatus and method concepts and embodiments are provided for control of fluid flow by force amplification syringe means. The concepts are particularly suited to surgical methods and apparatus for removing fluid from a patient or administering fluid to the patient, particularly at a fluid flow rate that is the most tolerable from the point of view of the patient.

9 Claims, 6 Drawing Figures

SYRINGE HOLDER DEVICE FOR CONTROLLED FORCE AMPLIFICATION SYRINGE FLUID FLOW

The present invention pertains to control of fluid flow by force amplification syringe means. The invention is particularly suited to surgical methods and apparatus for removing fluid from a patient or administering fluid to the patient, particularly at a fluid flow rate that is the most tolerable from the point of view of the patient.

BACKGROUND OF THE INVENTION

For the treatment of cancer by chemotherapy, a widely accepted practice involves a surgical procedure in which an indwelling catheter line or tubing is implanted in the patient with the distal terminus at the diseased organ site and the proximal terminus external to the body. For example, for cancer of the liver, the catheter line is established through the hepatic artery directly to the liver. Thus, by syringe fluid flow to the organ site, the required chemotherapeutic dosage regimen is accomplished at the target area via the installed catheter unit. Similarly, to maintain the patency of the catheter lumen, to prevent growth in, or plunging of the catheter, physiological saline is administered by syringe means. The procedure can be done in the hospital or on an out-patient basis, both for medication and for saline. For example, in a typical case, the schedule might call for a 90-cc. volume dosage of the medication every 3 weeks and a 5-cc. volume dosage of the saline solution twice daily. The procedures can be difficult due to the degree of force and dexterity required, especially when self-administered. Where nursing assistance is available, a common problem is that the pumping action by the operator may develop unduly high pressure peaks and linear flow rates that are excruciatingly painful to the patient.

Syringe holder apparatus of various kinds is known as described, for example, in U.S. Pat. Nos. 2,270,804; 2,491,978; 2,771,217; 3,993,064; and 4,465,478. In the usual case, however, such apparatus is complex, expensive and difficult to maintain in a clinical setting for purposes of sterility. Some devices are intended for table mounting and not to be hand-held. The art lacks syringe holder apparatus means that is simple, easy to load and manipulate, economical and therefore disposable after use.

It is therefore an object of the present invention to provide improved syringe holder apparatus means for controlled forced amplification of syringe fluid flow.

It is also an object to provide syringe holder apparatus that serves to minimize adverse fluid flow characteristics associated with patient trauma.

It is a further object to provide cost-efficient syringe holder apparatus that can be used in a clinical or out-patient setting and either re-sterilized for re-use or thrown away after single use or limited use.

These and other objects, features and advanages of the invention will become apparent from the following description.

SUMMARY AND DETAILED DESCRIPTION

In one preferred embodiment, the invention concerns a syringe holder for loading with a cylindrical syringe and for facilitating the axial advancement of the syringe barrel plunger from a retracted position to continuously advanced dispensing positions in a manner presently to be described. The syringe holder includes axially aligned barrel and plunger housing sections. The barrel housing, has the form of an open-sided open-ended part cylinder shell or cylinder section dimensioned to receive, support and stabilize the syringe barrel in co-axially mounted relation. The plunger housing has a hollow cylindrical form with an open end and a closed end; the housing contains an open zone dimensioned to receive the retracted plunger of the above-mentioned mounted syringe barrel. The closed housing end includes a central aperture to accomodate insertion therethrough of a spacing bar on an axial line within the plunger housing. The syringe holder also includes means for applying force against the head of the plunger comprising spacing bar torque means and a spacing bar. The bar has leading and trailing ends and a shank. The spacing shank and the aperture surfaces of the plunger housing are threaded for threadably engaging the spacing bar within the central aperture. Torquing the bar achieves controlled forward or rearward biasing movement of the leading end of the spacing bar with controlled force against a syringe plunger head located within the plunger housing. Preferably, the leading edge of the spacing bar comprises a flange reversely recessed and dimensioned at its forward surface such that the flange structure of a syringe plunger head can be removably inserted within the body of the flange to achieve a coupling effect therebetween for purposes of either aspirating or pumping. In a preferred embodiment of the syringe holder, the housing or barrel housing preferably, comprises slot means dimensioned to receive the flange structure of a syringe barrel and to thereby stabilize the same against axial dislocation. The plunger housing and barrel housing can be a single, unitary structure. In a preferred embodiment, the plunger housing comprises functionally matching half-cylinder parts such that the plunger housing can be assembled from the parts into a unitary closed cylindrical configuration. In one preferred form, the matching parts are unitarily joined at one side by hinge means. In another preferred form, the matching parts are separate and fastenably joinable together by suitable means such as fastening means, snap fasteners or clips, circumferential inelastic or elastic bands such as pressure-sensitive tape, metal bands, rubber bands and the like. In one preferred embodiment, the fasteners are located in matching relation on the mutually contacting edges of the half-cylinder parts. Preferably, the fasteners are molded as a single piece with each of the half-cylinder parts, made of pressure moldable structural polymeric plastic that distorts or flexes and has memory bias in the closed configuration.

In another aspect, the invention concerns a method for loading a syringe holder having the closed plunger housing as described, comprising assembling a loaded syringe plunger head-first into the plunger housing to a position where the syringe barrel is in a co-axially mounted relation with the barrel housing. By these means, the assembly can thereafter be held in one hand, leaving the other hand free for torquing the spacing bar to perform its function of applying force against the plunger head.

In a preferred method for loading a syringe holder having the open plunger housing as described, the procedure calls for assembling the spacing bar and the loaded syringe plunger head-first into the open half-cylinder part with the plunger head inserted within the body of the spacing bar flange to achieve a coupling effect therebetween for purposes of either aspirating or pumping. This is followed by assembling the matching half-cylinder parts into a unitary closed cylindrical configuration and securing the halves by suitable means such as clip means, bonding or the like. This procedure allows full visibility and complete ease of hand held operation for purposes both of aspiration and pumping.

The invention will be better understood by reference to preferred embodiments in the accompanying drawings wherein.

Figure 1:
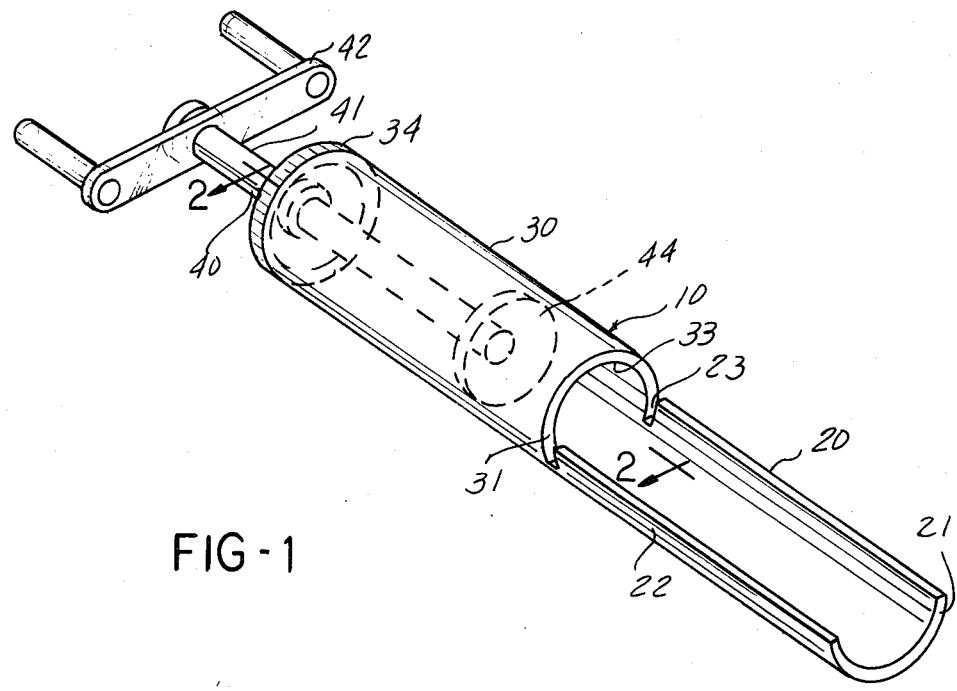
FIG. 1 is a view in perspective of a preferred syringe holder of the invention.
Figure 2:
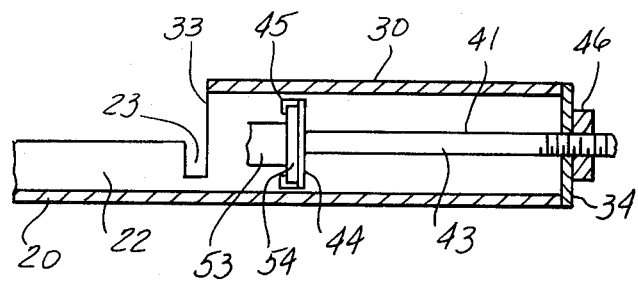
FIG. 2 is a fragmentary view partly in cross section, of the syringe holder taken on line 2—2 of FIG. 1.
Figure 3:
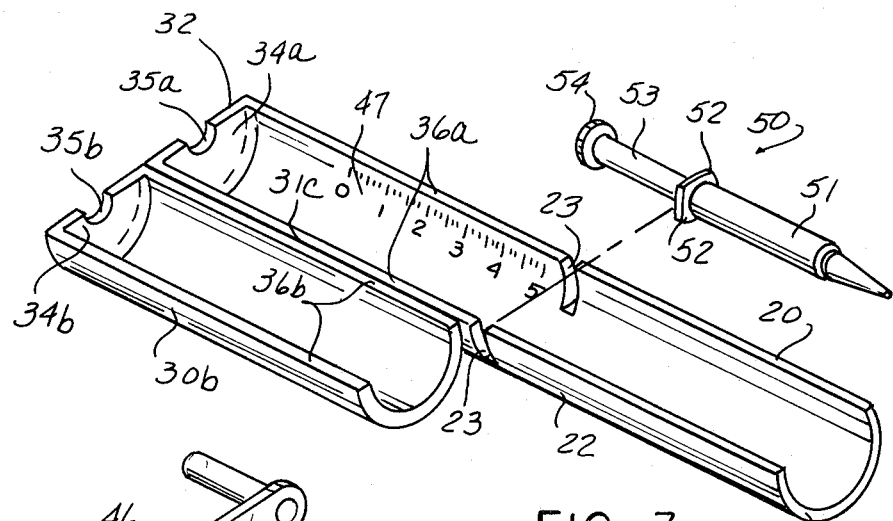
FIGS. 3 and 3a are each a view in perspective of components of a preferred syringe holder of the invention.

As shown in FIG. 1, the syringe holder 10 is a tubular member partly hollow having housings 20 and 30 respectively for the barrel 51 and retracted plunger 53 of a syringe 50 (FIG. 3). The barrel housing is integral with the plunger housing and has front and rear sections 21 and 22. A pair of slots 23 are located at the rear 22 of the barrel housing 20. The housing is dimensioned and shaped to co-axially match and receive the barrel 51 of a syringe with its flanges 52 firmly fitted into the slots 23 (FIG. 3) to keep the mounted barrel from axially dislocating. The plunger housing 30 has front and rear edges 31 and 32 with open and closed ends 33 and 34. The closed end 34, which has a central opening 35 (as seen in FIG. 3), may be integral with the housing or separate, as shown in FIGS. 1 and 2. The housing 30 is dimensioned to receive at its end 33 of a loaded syringe, the plunger 53. The syringe holder 10 includes a force control structure 40 for applying force to the flanged end 54 of a plunger. This includes a spacing bar 41, means 42 external to the plunger housing for torquing the bar, a spacing bar shank 43, a flange 44, and an end plate 46 (FIG. 2).

Figure 3A:
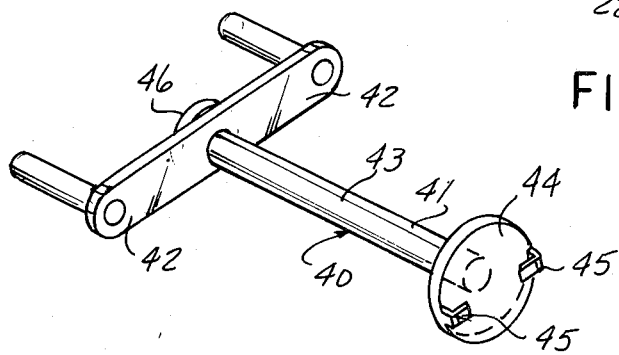
Figure 4:
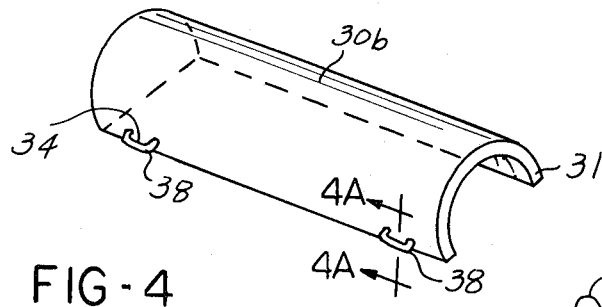
FIG. 4 is a pespective view of a detached half-cylinder part of a syringe holder plunger housing.
Figure 4A:
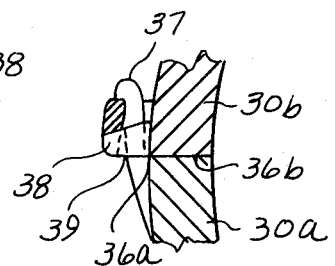
FIG. 4a is a fragmentary view partly in section taken on line 4a—4a of FIG. 4.

A preferred embodiment of a syringe holder, shown in FIG. 3, includes a plunger housing 30 with functionally matching half-cylinder sections 30a and 30b with matching side edges 36a, 36a and 36b, 36b. Two of the side edges 36a and 36b are joined by a lengthwise hinge 30c. The remaining two side edges 36a and 36b are joined by fasteners (not shown) which may be conventional. The closed ends 34a and 34b of the plunger housing sections are integral therewith and configured with central recesses 35a and 35b one of which serves as an indexing surface for mounting the shank 43 of a force controller 40 (FIG. 3a). The force control includes a spacing bar 41, a dual torquing arm and handle 42, and a shank 43. The shank terminates at its forward end in a flange 44 with retention fingers 45 spaced axially from the flange body at a distance slightly greater than the thickness of a syringe plunger flange 54 so that the latter can be fitted into the space to allow for controlled unitary forward and rearward axial movement of the two flanges 44 and 54. Another preferred embodiment, of which a half-cylinder component is shown in FIG. 4, is functionally similar to the embodiment shown in FIG. 3 except that the half-cylinder 30a and 30b lack the hinge 30c and are fastened together and prevented from separating at each of their side edges by a clip 37 and matching clip socket 38 shown in detail in FIG. 4a. The clip and clip socket are located in pairs on each edge 36a and 36b, are integral with their respective half-cylinders section. The clip 37 by its construction is resiliently biased away from the circumference of the cylinder wall whereas the clip socket has an opening 39 alongside the wall so that the two parts can be fastened together by compressing the clip and manually guiding it through the opening 39, and then allowing the clip to regain its bias in the locking position shown.

OPERATION OF THE SYRINGE HOLDER

To operate the syringe holder, preassembled as in FIG. 1 but with the spacing bar 41 in a retracted position and held in one hand, one inserts the loaded syringer, plunger head-first into co-axial position into the syringe holder, using the other hand. In this position, the barrel flanges 52 are located within the barrel housing slots 23. While the plunger housing is held in one hand (usually the left hand for right-handed persons), the other hand is used to turn the dual torquing arm and handle 42 in a rotation that causes the spacing bar 41 to contact and push the syringe plunger sufficiently forward to initiate delivery of the syringe content therefrom at a controlled rate. In a case where the syringe is connected to an implanted catheter line of the kind described above, the delivery may purposely be slow to assess whether the delivery (self-administered or otherwise) is comfortable for the patient. In such a case, the delivery rate may be 5cc. in a short period ranging, for example, from about one minute to about 20 minutes, as desired. The torquing force applied to the spacing bar resulting from a 2-inch arm (4-inch total for the dual arms 42) surprisingly has been found sufficient in an actual case to provide the force required for the mentioned atraumatic delivery.

To operate the syringe holder of FIG. 3, one holds the housing in one hand in the open position illustrated, and places or inserts the shank 43 of the force controller 40 into the axial recess 35a (the surface of which is threaded like that of the shank) so that the controller is in a stand-by position analogous to that shown in FIG. 1. In doing so, however, one advantageously is free to select the precise position of axial placement such that the spacing bar flange 44 will be placed in the housing at a point coinciding with what will be the trailing end of a given size of retracted syringe plunger to be loaded in the holder. To facilitate the location of the selected point, a numerically indexed scale 47 is provided to serve as a benchmark. In this way the retention fingers 45 will be correctly located to receive the flange 54 of a loaded syringe 50 (See FIG. 2). One then loads the open holder with a syringe placed with its flanges 52 and 54 nested respectively in the holder slots 23, 23 and fingers 45, 45. One next closes the open plunger housing and fastens the two halves (two piece or hinged) by suitable fastener means such as the clip-and-socket of FIGS. 4 and 4a, or by adhesive means or Velcro tape means, or by circumferential slip ring means (not shown) brought forwardly from the rearward shank portion. Thus the assembly is complete, and the syringe content can be dispensed in the manner described above. Similar considerations apply to the use of the holder for aspiration except that the point for location of the spacing flange on the scale 47 will be different.

Except as noted, the syringe holder in the described embodiments is preferably of one-piece molded clear plastic construction that may be sterilized by autoclaving or other suitable means. The plunger housing and end plate may suitably be in one piece or in two or more pieces joined together by any suitable means such as solvent bonding or adhesive bonding or by swaging or wedge locking. Also, the parts of the force controller where separate may be secured together by similar means. The clips 37 are preferably made of flexibly deformable plastic which is resilient, that is having a memory such that it can be deformed under manual pressure and yet can spontaneously regain its original shape in the at-rest position when such pressure is relieved. A suitable material, for example, is flexible polyvinyl chloride.

While the invention is described in detail in the foregoing specification, it will be realized by those skilled in the art that considerable variation can be made in such detail without departing from the spirit and scope of the claims which follow.

We claim:

1. A syringe holder for loading with a cylindrical syringe having a syringe barrel with a unitary flange structure and for facilitating the axial advancement of the syringe barrel plunger from a retracted position to continuously advanced dispensing positions, including axially aligned barrel and plunger housing sections, the barrel housing having the form of an open-sided open-ended part cylinder dimensioned to receive, support and stabilize the syringe barrel in coaxially mounted relation, the barrel housing comprising slot means dimensioned to receive the flange structure of a syringe barrel thus loaded into the holder and to thereby stabilize the barrel against axial dislocation with respect to the barrel housing, the plunger housing having cylindrical form with an open end and a closed end defining an open zone dimensioned to receive the retracted plunger of the loaded syringe barrel, said closed housing end including a central aperture to accommodate insertion therethrough of a spacing bar on an axial line within the plunger housing, and means for applying force against the head of the plunger comprising spacing bar torque means and a spacing bar having leading and trailing ends and a shank, the shank and the closed end of the plunger housing being threaded for threadably engaging the spacing bar within the central aperture such that torquing the bar achieves controlled biasing movement of the leading end of the spacing bar against the syringe plunger head located within the plunger housing.

2. A syringe holder according to claim 1 where the plunger housing comprises functionally matching half-cylinder parts such that the plunger housing can be assembled from the parts into a unitary closed cylindrical configuration.

3. A syringe holder according to claim 2 where the matching parts are unitarily joined at one side by hinge means.

4. A syringe holder according to claim 2 where the matching parts are separate and fastenably joinable.

5. A syringe holder according to claim 2 where the leading edge of the spacing bar comprises a flange reversely recessed and dimensioned at its forward surface such that the flange structure of a syringe plunger head can be removably inserted within the body of the flange to achieve a coupling effect therebetween for purposes of either aspirating or pumping.

6. A syringe holder according to claim 5 where the matching parts of the plunger housing are joined by hinge means.

7. A syringe holder according to claim 5 where the matching parts are separate and fastenably joinable.

8. A syringe holder according to claim 2 where the matching parts comprise tension fastening means.

9. A syringe holder according to claim 8 where the fastening means comprise polymeric plastic having memory bias in the closed configuration.

* * * * *